United States Patent
Zeng et al.

(10) Patent No.: US 9,828,499 B2
(45) Date of Patent: *Nov. 28, 2017

(54) ALKALINE-SWELLABLE EMULSION POLYMERS

(71) Applicant: Rohm and Haas Company, Philadelphia, PA (US)

(72) Inventors: Fanwen Zeng, Belle Mead, NJ (US); Sylvie Doulut, Cagnes sur Mer (FR)

(73) Assignee: ROHM AND HAAS COMPANY, Philadelphia, PA (US)

( * ) Notice: Subject to any disclaimer, the term of this patent is extended or adjusted under 35 U.S.C. 154(b) by 182 days.

This patent is subject to a terminal disclaimer.

(21) Appl. No.: 14/782,121

(22) PCT Filed: Apr. 4, 2014

(86) PCT No.: PCT/US2014/033006
§ 371 (c)(1),
(2) Date: Oct. 2, 2015

(87) PCT Pub. No.: WO2014/165777
PCT Pub. Date: Oct. 9, 2014

(65) Prior Publication Data
US 2016/0053103 A1    Feb. 25, 2016

(51) Int. Cl.
*C08F 220/06* (2006.01)
*C08F 220/10* (2006.01)
*C08L 33/08* (2006.01)
*A61K 8/81* (2006.01)

(52) U.S. Cl.
CPC ............ *C08L 33/08* (2013.01); *A61K 8/8152* (2013.01); *C08F 220/06* (2013.01); *A61K 2800/594* (2013.01); *C08L 2205/02* (2013.01)

(58) Field of Classification Search
CPC ..... A61K 8/8152; C08F 22/26; C08F 220/06; C08F 2800/20; C08F 2400/00; C08L 33/08
See application file for complete search history.

(56) References Cited

U.S. PATENT DOCUMENTS

| | | |
|---|---|---|
| 3,804,881 A | 4/1974 | Bassett et al. |
| 4,110,291 A | 8/1978 | Barabas et al. |
| 4,111,876 A | 9/1978 | Bailey et al. |
| 4,529,773 A | 7/1985 | Witiak et al. |
| 6,187,221 B1 | 2/2001 | Gore et al. |
| 7,173,083 B2 | 2/2007 | Scheerder et al. |
| 9,587,057 B2 * | 3/2017 | Zeng .................. C08F 2/00 |
| 2006/0182707 A1 | 8/2006 | Collin et al. |
| 2007/0213243 A1 | 9/2007 | Yao et al. |
| 2011/0319561 A1 | 12/2011 | Suau |

FOREIGN PATENT DOCUMENTS

| | | |
|---|---|---|
| CN | 1821377 A | 8/2006 |
| CN | 1944474 A | 4/2007 |
| CN | 102202639 A | 9/2011 |
| CN | 102906131 A | 1/2013 |
| EP | 1685827 A1 | 8/2006 |
| WO | 2012/044929 A2 | 4/2012 |
| WO | WO-2013088187 A1 * | 6/2013 |

* cited by examiner

*Primary Examiner* — Irina S Zemel
*Assistant Examiner* — Jeffrey S Lenihan
(74) *Attorney, Agent, or Firm* — Kenneth Crimaldi

(57) ABSTRACT

Emulsion polymer particles comprising from 25 to 45 wt % polymerized residues of at least one $C_3$-$C_6$ carboxylic acid monomer and from 0.1 to 2 wt % polymerized residues of at least one crosslinker, wherein the particles have a Tg which occurs over a range of at least 60° C.

8 Claims, No Drawings

ALKALINE-SWELLABLE EMULSION POLYMERS

BACKGROUND

This invention generally relates to alkaline-swellable emulsion polymers made using a power feed of monomers.

Polymers made using power feed of monomers are known. For example, U.S. Pat. No. 3,804,881 discloses polymers made using this process. However, the alkaline-swellable polymers disclosed in the present application, which are useful as rheology modifiers, are not known.

The problem solved by the present invention is to provide additional alkaline-swellable polymers for use as rheology modifiers.

STATEMENT OF THE INVENTION

The present invention is directed to emulsion polymer particles comprising from 25 to 45 wt % polymerized residues of at least one $C_3$-$C_6$ carboxylic acid monomer and from 0.1 to 2 wt % polymerized residues of at least one crosslinker, wherein the particles have a Tg which occurs over a range of at least 60° C.

The present invention is further directed to a method for producing the emulsion polymer particles by steps of: (a) providing a first monomer mixture comprising from 15 to 28 wt % of at least one $C_3$-$C_6$ carboxylic acid monomer; (b) providing a second monomer mixture comprising from 9 to 17 wt % of at least one $C_3$-$C_6$ carboxylic acid monomer; and (c) adding the first monomer mixture to a polymerization reactor while simultaneously adding the second monomer mixture to the first monomer mixture; wherein weight percentages are based on total weight of the first and second monomer mixtures.

DETAILED DESCRIPTION OF THE INVENTION

All percentages are weight percentages (wt %), all fractions are by weight and all temperatures are in ° C., unless otherwise indicated. Percentages of polymerized monomer residues in polymers are based on the entire weight of the solid polymer and percentages of monomers are based on total monomer weight. Measurements made at "room temperature" (room temp.) were made at 20-25° C. Any term containing parentheses refers, alternatively, to the whole term as if no parentheses were present and the term without them, and combinations of each alternative. Thus, the term "(meth)acrylic" refers to any of acrylic, methacrylic, and mixtures thereof. A "$C_3$-$C_6$ carboxylic acid monomer" is a mono-ethylenically unsaturated compound having one or two carboxylic acid groups, e.g., (meth)acrylic acid, maleic acid, fumaric acid, itaconic acid, maleic anhydride, crotonic acid, etc. Preferably, the acid monomer has three or four carbon atoms, preferably one carboxylic acid group, preferably (meth)acrylic acid, preferably methacrylic acid (MAA). Alkyl groups are saturated hydrocarbyl groups which may be straight or branched.

As used herein, unless otherwise indicated, the phrase "measured glass transition temperature" or "measured Tg" of a copolymer refers to a measured Tg, determined by modulated differential scanning calorimetry (MDSC) scanning from −150° C. to 150° C. while ramping temperature in a given sinusoidal modulation (oscillation) pattern overlaid on a conventional linear heating ramp at a ramp rate of 2.00° C./min to 150.00° C., taking the mid-point in the heat flow versus temperature transition as the Tg value. As used herein, the term "broad measured glass transition temperature (broad measured Tg)" refers to an MDSC glass transition wherein either the onset or final temperature of the recorded temperature curve are poorly defined. An example of a polymer having a broad measured Tg is a powerfeed emulsion copolymer. Preferably, the Tg of the particles occurs over a range of at least 65° C., preferably at least 70° C., preferably at least 75° C., preferably at least 80° C.

Crosslinkers are monomers having two or more non-conjugated ethylenically unsaturated groups. Preferred crosslinkers include, e.g., di- or tri-allyl ethers and di- or tri-(meth)acrylyl esters of diols or polyols (e.g., trimethylolpropane diallyl ether (TMPDAE) and trimethylolpropane trimethacrylate (TMPTMA)), di- or tri-allyl esters of di- or tri-acids, allyl (meth)acrylate, divinyl sulfone, triallyl phosphate, divinylaromatics (e.g., divinylbenzene). Preferably, the crosslinker has a molecular weight no greater than 800, preferably no greater than 700, preferably no greater than 600, preferably no greater than 500, preferably no greater than 400. Preferably, the molecular weight of the crosslinker divided by the number of ethylenically unsaturated groups is no greater than 150, preferably no greater than 140, preferably no greater than 130; preferably at least 50, preferably at least 65.

Preferably, the polymer particle is an acrylic polymer, i.e., one having at least 70 wt % polymerized residues of acrylic monomers, preferably at least 80 wt %, preferably at least 90 wt %, preferably at least 95 wt %, preferably at least 98 wt %, preferably at least 99 wt %. Acrylic monomers include (meth)acrylic acids and their $C_1$-$C_{22}$ alkyl or hydroxyalkyl esters; crotonic acid, itaconic acid, fumaric acid, maleic acid, maleic anhydride, (meth)acrylamides, (meth)acrylonitrile and alkyl or hydroxyalkyl esters of crotonic acid, itaconic acid, fumaric acid or maleic acid. The acrylic polymer may also comprise other polymerized monomer residues including, e.g., non-ionic (meth)acrylate esters, cationic monomers, monounsaturated dicarboxylates, vinyl esters of $C_1$-$C_{22}$ alkyl carboxylic acids, vinyl amides (including, e.g., N-vinylpyrrolidone), sulfonated acrylic monomers, vinyl sulfonic acid, vinyl halides, phosphorus-containing monomers, heterocyclic monomers, styrene and substituted styrenes. Preferably, the polymer contains no more than 3 wt % sulfur- or phosphorus-containing monomers, preferably no more than 2 wt %, preferably no more than 1 wt %, preferably no more than 0.5 wt %, preferably no more than 0.2 wt %.

Preferably, the polymer particles also comprise 54 to 74 wt % polymerized residues of at least one $C_1$-$C_{12}$ alkyl (meth)acrylate; preferably, at least 56 wt %, preferably at least 58 wt %, preferably at least 60 wt %, preferably at least 62 wt %; preferably no more than 72 wt %, preferably no more than 70 wt %, preferably no more than 68 wt % Preferably, the $C_1$-$C_{12}$ alkyl(meth)acrylate is limited to a $C_1$-$C_8$ alkyl(meth)acrylate, preferably a $C_2$-$C_8$ alkyl (meth) acrylate; preferably the $C_1$-$C_{12}$ alkyl(meth)acrylate is limited to a $C_1$-$C_{12}$ alkyl acrylate, preferably a $C_1$-$C_8$ alkyl acrylate, preferably a $C_2$-$C_8$ alkyl acrylate. Preferably the polymer particles comprise at least 27 wt % polymerized residues of at least one $C_3$-$C_6$ carboxylic acid monomer, preferably at least 29 wt %, preferably at least 31 wt %, preferably at least 33 wt %; preferably no more than 43 wt %, preferably no more than 41 wt %, preferably no more than 39 wt %, preferably no more than 37 wt %. Preferably the polymer particles comprise at least 0.3 wt % polymerized residues of at least one crosslinker, preferably at least 0.4 wt %, preferably at least 0.5 wt %; preferably no more than 2.5 wt %, preferably no more than 2 wt %, preferably no more than 1.5 wt %, preferably no more than 1.2 wt %, preferably no more than 1 wt %, preferably no more than 0.9 wt %, preferably no more than 0.8 wt %.

Preferably, the polymer particles comprise polymerized residues of a lipophilic monomer having the structure $H_2C=C(R)C(O)X(CH_2CH_2O)_n(CH(R')CH_2O)_mR"$, wherein X is O or NH, R is hydrogen or methyl, R' is methyl or ethyl; R" is $C_8$-$C_{22}$ alkyl, $C_8$-$C_{16}$ alkylphenyl or $C_{13}$-$C_{36}$ aralkylphenyl; n is an average number from 6-100 and m is an average number from 0-50, provided that n≥m and m+n is 6-100. Preferably, X is O. Preferably, the polymer particles comprise from 0.2 to 10 wt % polymerized residues of monomers of structure $H_2C=C(R)C(O)X(CH_2CH_2O)_n(CH(R')CH_2O)_mR"$, preferably from 0.3 to 8 wt %, preferably from 0.5 to 5 wt %, preferably from 0.5 to 4 wt %, preferably from 1 to 4 wt %. Preferably, R" is $C_8$-$C_{22}$ alkyl, preferably $C_{10}$-$C_{22}$ alkyl, preferably $C_{12}$-$C_{20}$ alkyl. Preferably, n is 15-30 and m is 0-5; preferably n is 18-25 and m is 0-3; preferably n is 18-25 and m is 0-2; preferably R' is methyl. Preferably, R is methyl. Preferably, R" is $C_{12}$-$C_{22}$ alkyl, n is 15-30 and m is 0-5; preferably, R" is $C_{12}$-$C_{22}$ alkyl, n is 18-25, m is 0-3 and R is methyl.

Preferably, the polymer particles are provided as an aqueous composition containing the polymer as discrete particles dispersed in an aqueous medium, i.e., a polymer latex. In this aqueous dispersion, the average particle diameter of the polymer particles preferably is in the range from 50 to 2000 nm, preferably from 100 to 1000 nm, preferably from 150 to 800 nm. The level of polymer particles in the aqueous dispersion is typically in the range of from 15 to 60 wt %, preferably 25 to 50 wt %, based on the weight of the aqueous dispersion. Preferably, the percentage of crosslinker and the acid monomer content increase continuously from particle centers to particle surfaces.

In describing the method of this invention, percentages of monomers are based on the total monomer weight. Preferably, the first monomer mixture further comprises from 54 to 74 wt % polymerized residues of at least one $C_1$-$C_{12}$ alkyl(meth)acrylate; preferably, at least 56 wt %, preferably at least 58 wt %, preferably at least 60 wt %, preferably at least 62 wt %; preferably no more than 72 wt %, preferably no more than 70 wt %, preferably no more than 68 wt %. Preferably, the $C_1$-$C_{12}$ alkyl(meth)acrylate is limited to a $C_1$-$C_8$ alkyl(meth)acrylate, preferably a $C_2$-$C_8$ alkyl(meth) acrylate; preferably the $C_1$-$C_{12}$ alkyl(meth)acrylate is limited to a $C_1$-$C_{12}$ alkyl acrylate, preferably a $C_1$-$C_8$ alkyl acrylate, preferably a $C_2$-$C_8$ alkyl acrylate. Preferably the first monomer mixture comprises at least 17 wt % of at least one $C_3$-$C_6$ carboxylic acid monomer, preferably at least 18 wt %, preferably at least 19 wt %, preferably at least 20 wt %; preferably no more than 25 wt %, preferably no more than 24 wt %, preferably no more than 23 wt %, preferably no more than 22 wt %. Preferably, the first monomer mixture further comprises from 0.1 to 2 wt % polymerized residues of at least one crosslinker. Preferably, the first monomer mixture comprises at least 0.2 wt % of at least one crosslinker, preferably at least 0.3 wt %, preferably at least 0.4 wt %, preferably at least 0.5 wt %; preferably no more than 2.5 wt %, preferably no more than 2 wt %, preferably no more than 1.5 wt %, preferably no more than 1.2 wt %, preferably no more than 1 wt %, preferably no more than 0.9 wt %, preferably no more than 0.8 wt %.

Preferably, the second monomer mixture comprises at least 10 wt % of at least one $C_3$-$C_6$ carboxylic acid monomer, preferably at least 11 wt %, preferably at least 12 wt %; preferably no more than 16 wt %, preferably no more than 15 wt %, preferably no more than 14 wt %. Preferably, the second monomer mixture further comprises from 0.1 to 2 wt % polymerized residues of at least one crosslinker. Preferably, the second monomer mixture comprises at least 0.2 wt % of at least one crosslinker, preferably at least 0.3 wt %, preferably at least 0.4 wt %, preferably at least 0.5 wt %; preferably no more than 2.5 wt %, preferably no more than 2 wt %, preferably no more than 1.5 wt %, preferably no more than 1.2 wt %, preferably no more than 1 wt %, preferably no more than 0.9 wt %, preferably no more than 0.8 wt %. Preferably, the second monomer mixture further comprises up to 15 wt % of monomers which are not crosslinkers, preferably up to 10 wt %, preferably up to 8 wt %. Preferably, the monomers in the second monomer mixture comprise no more than 5 wt % $C_1$-$C_{12}$ alkyl(meth) acrylate(s), preferably no more than 3 wt %, preferably no more than 2 wt %, preferably no more than 1 wt %, preferably no more than 0.5 wt %, preferably no more than 0.2 wt %.

Preferably, the first monomer mixture comprises a lipophilic monomer having the structure $H_2C=C(R)C(O)X(CH_2CH_2O)_n(CH(R')CH_2O)_mR"$, wherein X is O or NH, R is hydrogen or methyl, R' is methyl or ethyl; R" is $C_8$-$C_{22}$ alkyl, $C_8$-$C_{16}$ alkylphenyl or $C_{13}$-$C_{36}$ aralkylphenyl; n is an average number from 6-100 and m is an average number from 0-50, provided that n≥m and m+n is 6-100. Preferably, X is O. Preferably, the first monomer mixture comprises from 0.2 to 10 wt % of monomers of structure $H_2C=C(R)C(O)X(CH_2CH_2O)_n(CH(R')CH_2O)_mR"$, preferably from 0.3 to 8 wt %, preferably from 0.5 to 5 wt %, preferably from 0.5 to 4 wt %, preferably from 1 to 4 wt %. Preferably, R" is $C_8$-$C_{22}$ alkyl, preferably $C_{10}$-$C_{22}$ alkyl, preferably $C_{12}$-$C_{20}$ alkyl. Preferably, n is 15-30 and m is 0-5; preferably n is 18-25 and m is 0-3; preferably n is 18-25 and m is 0-2; preferably R' is methyl. Preferably, R is methyl. Preferably, R" is $C_{10}$-$C_{22}$ alkyl, n is 15-30 and m is 0-5; preferably, R" is $C_{12}$-$C_{22}$ alkyl, n is 18-25, m is 0-3 and R is methyl.

Preferably, the first monomer mixture comprises a nonionic water-soluble monomer, preferably having the structure $H_2C=C(R)C(O)X(CH_2CH_2O)_n(CH(R')CH_2O)_mR"$, wherein X is O or NH, R is hydrogen or methyl, R' is methyl or ethyl; R" is methyl or ethyl; n is an average number from 6-100 and m is an average number from 0-50, provided that n≥m and m+n is 6-100. Preferably, X is O. Preferably, the first monomer mixture comprises from 0.2 to 10 wt % of monomers of structure $H_2C=C(R)C(O)X(CH_2CH_2O)_n(CH(R')CH_2O)_mR"$, preferably from 0.5 to 8 wt %, preferably from 1 to 7 wt %, preferably from 2 to 7 wt %, preferably from 3 to 7 wt %. Preferably, R" is methyl. Preferably, n is 15-30 and m is 0-5; preferably n is 18-25 and m is 0-3; preferably n is 18-25 and m is 0-2; preferably R' is methyl. Preferably, R is methyl. Preferably, R" is methyl, n is 15-30 and m is 0-5; preferably, R" is methyl, n is 18-25, m is 0-3 and R is methyl. Other preferred nonionic water-soluble monomers include acrylamide, N-methyl or -ethyl acrylamides, N,N-dimethyl or -diethyl acrylamides, polyethylene glycol (meth)acrylate N-vinylacetamide, N-methyl-N-vinylacetamide, N-vinylformamide, N-methyl-N-vinylformamide, N-vinyl lactams hydroxyethyl acrylate, hydroxypropyl acrylate, hydroxyethyl methacrylate, hydroxypropyl methacrylate, and mixtures thereof. An especially preferred nonionic water-soluble monomer is methoxy-poly(ethylene glycol) monomethacrylate.

Preferably less than 10 wt % of the monomers is in the polymerization reactor prior to addition of the first monomer mixture, preferably less than 7 wt %, preferably less than 5 wt %, preferably less than 3 wt %, preferably less than 2 wt %, preferably less than 1 wt %. Preferably, the monomers are added to the reactor over a period of time from 60 to 240 minutes, preferably from 80 to 160 minutes, preferably 90 to 150 minutes. Preferably the time of addition of the second monomer mixture to the first monomer mixture is from 50 to 120% of the time of addition of the first monomer mixture to the polymerization reactor, preferably from 75 to 100%, preferably from 90 to 100%. Preferably, addition of the second monomer mixture to the first monomer mixture begins no later than addition of the first monomer mixture to the polymerization reactor, preferably at the same time.

Typical aqueous emulsion polymerization techniques are suitable for use in the method of this invention. Aqueous emulsion polymerization processes typically are conducted in an aqueous reaction mixture, which contains at least one monomer and various synthesis adjuvants such as the free radical sources, buffers, and reductants in an aqueous reaction medium. A chain transfer agent may used to limit molecular weight, preferably a mercaptan, preferably a $C_8$-$C_{12}$ alkyl mercaptan. The aqueous reaction medium is the continuous fluid phase of the aqueous reaction mixture and contains greater than 50 wt % water and optionally one or more water miscible solvents, based on the weight of the aqueous reaction medium. Suitable water miscible solvents include methanol, ethanol, propanol, acetone, ethylene glycol ethyl ethers, propylene glycol propyl ethers, and diacetone alcohol. Preferably, the aqueous reaction medium contains at least 90 wt % water, preferably at least 95 wt % water, preferably at least 98 wt % water, based on the weight of the aqueous reaction medium.

The emulsion polymer particles of this invention are useful in a variety of thickened aqueous formulations as described above, including body washes, shampoos, personal care cleansers; liquid soap (e.g., liquid hand soap), cleaning formulations for fabric (e.g., laundry detergent), dishes, and hard surfaces; liquid auto-dish detergent, manual dish detergent, spot-pretreaters, oven cleaners, and glass/window cleaners, conditioners (e.g., hair and skin), two-part hair dyes, hair gels; hair-styling cream, paste or gum; mousses, permanent waving formulations, tanning lotions, sunscreens and skin lotions. The polymer also is useful as an emulsifier, e.g., in surfactant-free systems (e.g., creams or lotions). A formulation thickened with the polymer particles can be used to suspend beads, silicones, silica, emollient oils, organic and inorganic uv filters and abrasives. The polymer particles can be used in combination with other rheology modifiers. When the particles are swollen through contact with alkali it often is not possible to distinguish individual particles in the gel-like system which is formed.

A thickened aqueous formulation contains from 0.1 to 5 wt % of the polymer particles, calculated on a polymer solids basis relative to the entire weight of the aqueous formulation. Preferably, a thickened aqueous formulation contains at least 0.3 wt % of the polymer particles, preferably at least 0.5 wt %, preferably at least 0.7 wt %, preferably at least 0.9 wt %, preferably at least 1.1 wt %, preferably at least 1.3 wt %, preferably at least 1.5 wt %. Preferably, a thickened aqueous formulation contains no more than 4 wt % of the polymer particles, preferably no more than 3 wt %, preferably no more than 2.5 wt %, preferably no more than 2 wt %. Preferably, the thickened aqueous composition also contains at least one surfactant, preferably at least two surfactants. Preferred anionic surfactants for use in the practice of the invention may be selected from the $C_8$ to $C_{18}$ fatty acids or their water soluble salts, water soluble sulfates or ether sulfates of $C_8$ to $C_{18}$ alcohols, sulfonated alkylaryl compounds such as, for example, dodecylbenzene sulfonate, alkylphenoxy polyethoxy ethanols, for example with $C_7$ to $C_{18}$ alkyl groups and 9 to 40 or more oxyethylene units, ethylene oxide derivatives of long chain carboxylic acids, for example of lauric, myristic, palmitic or oleic acids, ethylene oxide derivatives of long chain alcohols, for example of lauryl or cetyl alcohols, alkanolamides and polyglucosides, for example the alkyl polyglucosides, and surfactants derived from amino acids, e.g. glutamates. Especially preferred surfactants include, e.g., sodium laureth sulfate (SLES) and cocamidopropyl betaine (CAPB). Preferably the total amount of surfactants in the aqueous composition is from 5 wt % to 30 wt %; preferably at least 8 wt %, preferably at least 10 wt %, preferably at least 12 wt %; preferably no more than 25 wt %, preferably no more than 22 wt %, preferably no more than 20 wt %. Preferably, the pH of the thickened aqueous composition is from 3 to 12, preferably from 3.5 to 10, preferably from 3.5 to 8, preferably from 4 to 7.

Preferably, the polymer particles described in this invention provide clarity and suspension properties for the thickened aqueous composition, i.e., turbidity of the sample is less than 50 NTU, using specifications in U.S. Environmental Protection Agency method 180.1 (Nephelometric Method). Suspending refers to the even dispersion of particulate or solid material, liquid material, or air throughout the continuous phase of the formulation. Failure of suspension is marked by phase separation of the dispersed material from the continuous phase under a range of storage temperature conditions.

A particular aqueous composition in which the polymer of this invention is useful is a body wash. Typical components of a body wash, in addition to the polymer thickener and surfactant mentioned previously, include sufficient base or acid to attain a pH of 4-7, preferably 4.5-6.8, preferably 4.5 to 5.5, preferably 5-6.6; and optional ingredients, including silicones, pearlizing agents, vitamins, oils, fragrances, dyes, biocides, and insoluble beads made from a variety of materials, including polyolefins, e.g., polyethylene and polystyrene; gelatin; mica; encapsulated oil or vitamin beads; and Jojoba wax beads. Preferably, the amount of beads is from 0.1% to 2%, more preferably from 0.2% to 1%. Preferably, the average radius of the beads is from 0.1 mm to 10 mm. Typically, the surfactant used is a mixture of an anionic surfactant and an amphoteric surfactant, preferably from 8% to 16% of an anionic surfactant and from 1% to 5% of an amphoteric surfactant.

A second particular aqueous composition in which the polymer of this invention is useful is a shampoo. Typical components of a conditioning shampoo, in addition to the polymer thickener and surfactant mentioned previously, include sufficient base to attain a pH of 4-7, preferably 4-6, preferably 4.7-7.0. One particular embodiment of the invention is a conditioning shampoo containing a dispersed silicone, and optional ingredients, including pearlizing agents and zinc pyrithione or other anti-dandruff agents.

A third aqueous composition in which the polymer of this invention is useful is a hard surface cleaner. Typical components of a hard surface cleaner in addition to the polymer thickener and surfactant mentioned previously, include sufficient base to achieve a pH of 9-12, and optional ingredients including solvents, salts, fragrances, and dyes.

Preferably, a thickened aqueous composition is produced by neutralizing the emulsion polymer to a pH in the range from 6.5 to 8, preferably from 7 to 7.5, preferably from 7 to 7.5; and then acidifying to a pH in the range from 4 to 6, preferably from 4.5 to 5.5, preferably from 4.8 to 5.3. Suitable bases to neutralize the formulation include mineral bases such as sodium hydroxide and potassium hydroxide; ammonium hydroxide, and organic bases such as mono-, di- or tri-ethanolamine; preferably alkali metal hydroxides; preferably sodium or potassium hydroxide; preferably sodium hydroxide. Mixtures of bases may be used. Suitable acids to acidify the formulation include mineral acids such as hydrochloric acid, phosphoric acid, and sulfuric acid, and organic acids such as acetic acid; preferably carboxylic acids; preferably citric acid. Mixtures of acids may be used.

The composition of the present invention optionally may include other ingredients, e.g., salts, co-rheology modifiers (e.g. LAPONITE clay, cellulosics, carrageenan, xanthan, PEG-150 distearate (ACULYN 60 rheology modifier), PEG-150 pentaerythrityl tetrastearate, other associative or non-associative acrylic rheology modifiers such as acrylates copolymer, derivatives of acrylates copolymer, ACULYN 33 rheology modifier, ACULYN 22 rheology modifier, ACULYN 28 rheology modifier, Acrylates/Beheneth-25 Methacrylate Copolymer, derivatives of Acrylates/Beheneth-25 Methacrylate Copolymer, and ACULYN 88 rheology modifier, CARBOPOL Aqua-SF1, CARBOPOL Aqua 30, and CARBOPOL Ultrez-21, other acrylic or urethane polymers like ACULYN 44 rheology modifier or ACULYN 46 rheology modifier, organic or inorganic particles (including, for example, abrasives, beads, mica, encapsulated oil beads), silicones, pearlizing agents, dispersed liquids, dispersants, soluble or dispersed biocides, vitamins, humectants, enzymes, bleach, emollient, fragrance, dyes, thioglycolic acid, UVA and UVB absorbers, infrared absorbers, etc. Insoluble materials which may be suspended in the aqueous composition include clay, beads, wax, gelatin and other particulate materials.

EXAMPLES

In the following examples, the following terms and test procedures are used:
BA=butyl acrylate
MAA=methacrylic acid
EHA=2-ethylhexyl acrylate
EA=ethyl acrylate
Lipo1 is a lipophilically modified monomer having a linear saturated $C_{16-18}$ alkyl group connected through from 18 to 26 oxyethylene residues to a methacryloyl group.
Lipo2 is a lipophilically modified monomer having a linear saturated $C_{10}$-$C_{14}$ alkyl group connected through 20-28 oxyethylene residues to a methacryloyl group.
TMPDE: trimethylolpropane diallyl ether
SR399:
TMPTMA=trimethylolpropane trimethacrylate
TMPDAE=(ttrimethylolpropane diallylether)
SLES=sodium laureth sulfate
CAPB=cocamidopropyl betaine Example 1

To a 3-liter, 4-necked round bottom flask equipped with a mechanical stirrer, thermocouple, condenser and nitrogen sparge was added 729 μm of deionized water and 2 μm of sodium lauryl sulfate. The reactor was purged with nitrogen and warmed to 90° C. Separately, 1) a monomer emulsion (A) was prepared from 556 μm of deionized water, 25 μm of sodium lauryl sulfate, 458 μm of EA, 149 μm of MAA. 2) Monomer emulsion additive (B) was prepared by mixing 5.3 μm of TMPTA and 93 g of MAA. 3) Initiator solution C1 was prepared by dissolving 0.4 μm of ammonium persulfate in 19 μm of deionized water. 4) Initiator solution C2 was prepared by dissolving 0.7 μm of ammonium persulfate in 42 μm of deionized water. At ~90° C. reactor temperature, the reactor was charged with initiator solution C1. Then monomer emulsion (A) was charged into reactor while Monomer emulsion additive (B) was charged simultaneously to monomer emulsion (A). The rate was controlled so that the both feeds finished in 120 min. Separately, Initiator solution C2 was fed into the reactor in 120 min. After these additions were completed, the monomer emulsion and initiator feed lines were rinsed with deionized water followed with monomer chasing with free radical catalyst and activator. The resulting latex was filtered and analyzed for % solids, pH, residual monomer, particle size, gel content and viscosity.

Comparative Example 1

To a 3-liter, 4-necked round bottom flask equipped with a mechanical stirrer, thermocouple, condenser and nitrogen sparge was added 350 μm of deionized water and 2 μm of sodium lauryl sulfate. The reactor was purged with nitrogen and warmed to 90° C. Separately, 1) a monomer emulsion (A) was prepared from 935 μm of deionized water, 25 μm of sodium lauryl sulfate, 457 μm of EA, 242 μm of MAA and 5.3 μm of TMPTA. 3) Initiator solution C1 was prepared by dissolving 0.4 μm of ammonium persulfate in 19 μm of deionized water. 4) Initiator solution C2 was prepared by dissolving 0.7 μm of ammonium persulfate in 42 μm of deionized water. At ~90° C. reactor temperature, the reactor was charged with initiator solution C1. Then monomer emulsion (A) was charged into reactor. The rate was controlled so that the feed finished in 120 min. Separately, Initiator solution C2 was fed into the reactor in 120 min. After these additions were completed, the monomer emulsion and initiator feed lines were rinsed with deionized water followed with monomer chasing with free radical catalyst and activator. The resulting latex was filtered and analyzed for % solids, pH, residual monomer, particle size, gel content and viscosity.

Examples 2-12

Polymer samples 2-12 were prepared according to the procedure as described in Example 1 except the composition changes as described in Table 1.

Example 13

To a 3-liter, 4-necked round bottom flask equipped with a mechanical stirrer, thermocouple, condenser and nitrogen sparge was added 545 μm of deionized water and 2 μm of sodium lauryl sulfate. The reactor was purged with nitrogen and warmed to 90° C. Separately, 1) a monomer emulsion (A) was prepared from 556 μm of deionized water, 25 μm of sodium lauryl sulfate, 458 μm of EA, 149 μm of MAA and 5.3 μm of TMPTA. 2) Monomer emulsion additive (B) was prepared by mixing 93 g of MAA and 19 μm of deionized water. 3) Initiator solution C1 was prepared by dissolving 0.4 μm of ammonium persulfate in 19 μm of deionized water. 4) Initiator solution C2 was prepared by dissolving 0.7 μm of ammonium persulfate in 42 μm of deionized water. At ~90° C. reactor temperature, the reactor was charged with initiator solution C1. Then monomer emulsion (A) was charged into reactor while Monomer emulsion additive (B) was charged simultaneously to monomer emulsion (A). The rate was controlled so that the both feeds finished in 120 min. Separately, Initiator solution C2 was fed into the reactor in 120 min. After these additions were completed, the monomer emulsion and initiator feed lines were rinsed with deionized water followed with monomer chasing with free radical catalyst and activator. The resulting latex was filtered and analyzed for % solids, pH, residual monomer, particle size, gel content and viscosity.

Comparative Example 1

Prepared according to the procedure as described in Example 1 except the composition changes as described in Table 1.

TABLE 1

Polymers from Examples (E) made with power feed of cross-linker and 38% of total MAA and from a Comparative Example (CE) made by conventional polymerization

| Polymer | Polymer composition |
|---------|---------------------|
| E 1     | 65EA/35MAA//0.75% TMPTA |
| CE 1    | 65EA/35MAA//0.75% TMPTA |
| E 2     | 65EA/5EHA/35MAA//0.75% TMPTA |
| E 3     | 65EA/5BA/35MAA//0.75% TMPTA |
| E 4     | 65EA/35MAA//0.56% TMPTA |
| E 5     | 65EA/35MAA//0.94% TMPTA |
| E 6     | 64EA/1 Lipo-1/35MAA//0.75% TMPTA |
| E 7     | 64EA/1 Lipo-2/35MAA//0.75% TMPTA |
| E 8     | 64.5EA/0.5 Lipo-2/35MAA//0.75% TMPTA |
| E 9     | 62.5EA/2.5 MPEG750/35MAA//0.75% TMPTA |
| E 10    | 60EA/5 MPEG750/35MAA//0.75% TMPTA |
| E 11    | 65EA/35MAA//1.25% TMPTMA |
| E 12    | 65EA/35MAA//0.1% TMPDAE |
| E13     | 65EA/35MAA//0.75% TMPTA |

Examples 11-12

Procedure for measuring the aqueous neutralized solution properties (viscosity and turbidity) as summarized in Table 2

Solublized viscosity procedure for 1% polymer active:
1. Weigh out sufficient polymer example to have 1.0% polymer in final formulation.
2. Predilute with DI water to make 500 g solution.
3. Add 4.2 g of 20% w/w Sodium Hydroxide solution in water and stir efficiently with overhead stirrer until homogenous.
4. Measured pH should fall into 7.2 to 7.5 ranges. Adjust with 20% NaOH if necessary
5. Measure viscosity at 30 rpm using Brookfield viscometer with correspondent spindles to obtain measurements with at least at 10% of scale.
6. Transfer sample into 1 oz vial for turbidity measurement Solublized viscosity procedure for 2.5% polymer active:
1. Weigh out sufficient polymer example to have 2.5% polymer in final formulation.
2. Predilute with DI water to make 500 g solution.
3. Add 3.5 g of 20% w/w Sodium Hydroxide solution in water and stir efficiently with overhead stirrer until completely homogenous.
4. Measured pH should fall into 6.4 to 6.8 ranges. Adjust with 20% NaOH if necessary
5. Measure viscosity at 30 rpm using Brookfield viscometer with correspondent spindles to obtain measurements at least at 10% of scale
6. Transfer sample into 1 oz vial for turbidity measurement Turbidity Measurement:
1. Spin 1 oz vials with samples on centrifuge at 3500 rpm for 30 min
2. Measure turbidity on Turbidity meter.

TABLE 2

Aqueous neutralized solution property (viscosity and turbidity) of Polymer samples 1-13 and Comparative examples 1.

| | aqueous neutralized solution property with 2.5% polymer | | aqueous neutralized solution property with 1% polymer | |
|---|---|---|---|---|
| Polymer | viscosity (cps, 30 rpm) | turbidity (NTU) | viscosity (cps, 30 rpm) | turbidity (NTU) |
| E 1  | 7960 | 30.1  | 2460 | 2.85 |
| CE 1 | 3132 | 16.5  | 1340 | 19.4 |
| E 2  | 7920 | 29.7  | 3820 | 4.3  |
| E 3  | 7880 | 47.30 | 3860 | 2.86 |
| E 4  | 6420 | 22    | 2280 | 2.2  |
| E 5  | 8260 | 23.10 | 3920 | 3.21 |
| E 6  | 9100 | 35.30 | 3540 | 2.62 |
| E 7  | 9720 | 7.38  | 4620 | 3.87 |
| E 8  | 6360 | 16.50 | 3460 | 2.89 |
| E 9  | 9960 | 14.7  | 4400 | 3.28 |
| E 10 | 8820 | 18.10 | 4660 | 3.64 |
| E 11 | 5180 | 21.2  | 1116 | 1.54 |
| E 12 | 7280 | 23.0  | 1908 | 1.42 |
| 13   | 9000 | 10.1  | 4740 | 6.8  |

Overall, polymer examples 1-13 gave a much higher aqueous solution viscosity than the corresponding comparative example 1.

Formulation Examples (Table 3)

A. Procedure for Preparation of Personal Care Formulations:
1. Weigh out sufficient polymer samples to have 1.8-2.2% polymer in final formulation. Predilute with deionized water.
2. Add tetrasodium salt of ethylenediaminetetraacetic acid (VERSENE 100 XL, available from The Dow Chemical Company) to have 0.1% active ingredient in final formulation.
3. Add sodium laureth sulfate (EMPICOL ESB-70, available from Hunstman) to have 12.5% active ingredient in final formulation.
4. Add cocamidopropyl betaine (EMPIGEN BS/FA, available from Hunstman) to have 2.5% active ingredient in final formulation.
5. Adjust pH of formulation to above pH 7 with 30% NaOH solution.
6. Adjust pH back to specification with citric acid.
7. Add methylisothiazolinone (and) phenoxyethanol (NEOLONE PE, available from The Dow Chemical Company)
8. Add deionized water to total volume.

B. Formulation Variable Parameters:
sodium laureth sulfate (SLES) and cocamidopropyl betaine (CAPB) ratio and levels range as follow:

| | SL-2EO-S | SL-1EO-S | CAPB | Ratio |
|---|---|---|---|---|
| Formulation 5  | 12.5 |      | 2.5 | 5/1    |
| Formulation 13 | 6.25 | 6.25 | 2.5 | 5/1    |
| Formulation 9  | 8.3  |      | 1.7 | 4.9/1  |
| Formulation 10 | 11   |      | 4   | 2.75/1 |
| Formulation 12 | 16.5 |      | 3.5 | 4.7/1  | polymer concentration ranges from 1.4% to 2.2% active ingredient pH ranges from 4.5 to 7.0

C. Viscosity Measurements

Rheology analyses were conducted using two different equipments:
1 Using a TA Instrument AR 1000 rheometer at 20° C. with a 40 mm 4° acrylic cone. A standard steady state flow from low to high shear stress method was used for analysis with shear stress ramp from 0.006 Pa to 1000 Pa. Rheological profiles are run on samples aged of 24 hours at minimum and stored at room temperature or at 40° C. Ellis model was used to provide Zero Stress Viscosity (ZSV.
2 Using a LV Brookfield rheometer at 23° C. with spindle 4. Viscosities are reported in cPs at 12 or 60 rpm and correspond to viscosities of samples aged between 2 and 7 days stored at room temperature.

D. Clarity Evaluations

Clarity was assessed using two different techniques:
1 Using a HACH 18900-00 Turbidimeter and 1 cm cylindric glass sample cells. Clarity is reported in NTU values.
2 Using a HACH DR2000 spectrophotometer and 2.2 cm squared glass cells. Clarity is reported in Abs values at 320 nm or 400 nm.

E. Suspending Properties Evaluation

Suspension was evaluated in different ways:
1 Looking at beads and/or air bubbles suspension and stability over at minimum 4 weeks at the test temperature was reported as a "Pass" test result. Jojoba ester beads (Lapis 28/60 from Florabeads) were used. Air bubbles were manually introduced in samples (bubble size expected to be randomly distributed).
2 Zero Stress Values (Ellis Model) above F. Miscellaneous:

pH adjustments and values were performed using a SCHOTT CG-837 pH meter at room temperature.

Heat ageing tests on neat polymers or formulation samples with suspended beads or air bubbles were performed using a PROLABO EB Oven, model RA 6015, with temperature controlled at 40+/−2° C.

TABLE 3

Personal care formulation properties (zero-stress viscosity, turbidity) of various polymer examples at pH of 5 and 6.5.

| Polymer | pH | Zero Stress Viscosity | NTU | Abs (320 mm) | Abs (400 nm) |
|---|---|---|---|---|---|
| 1 | 5 | 90540 | 19.5 | 0.285 | 0.152 |
|   | 6.5 | 15400 | 16.2 | 0.278 | 0.142 |
| CE1 | 5 | 56840 | 115.6 |  |  |
|   | 6.5 | 5083 | 5.8 |  |  |
| 2 | 5 |  | 21.2 | 0.364 | 0.195 |
|   | 6.5 |  | 10.7 | 0.262 | 0.115 |
| 3 | 5 | 246300 | 27.3 | 0.395 | 0.206 |
|   | 6.5 |  | 14.2 | 0.314 | 0.139 |
| 4 | 5 | 88130 | 16.7 | 0.288 | 0.133 |
|   | 6.5 | 27100 | 17.7 | 0.282 | 0.127 |
| 5 | 5 | 873000 | 56.5 | 0.872 | 0.602 |
|   | 6.5 | 185800 | 39.4 | 0.404 | 0.243 |
| 6 | 5 | 198000 | 21.8 | 0.341 | 0.166 |
|   | 6.5 | 16510 | 21.6 | 0.350 | 0.169 |
| 13 | 5 | 266600 | 67.3 | 0.897 | 0.644 |
|   | 6.5 | 135400 | 23.7 | 0.309 | 0.181 |

Overall, in comparison with comparative example 1 in personal care formulation, polymer examples 1-13 lead to a higher zero stress viscosity at both pHs.

Measurement of Glass Transition Temperature.

Glass transition temperatures (Tg) were measured using TA instruments model 2920 Differential Scanning calorimeter either with conventional (20° C./min ramp rate) or modulated temperature ramp test method.

TABLE 4

Glass transition temperature of polymer examples

| Polymer sample | Glass transition temperature |
|---|---|
| Comparative example 1 | Narrow heat transition (Tg) from 55° C. to 90° C. |
| Polymer example 13 | Broad heat transition (Tg) from 31° C. to 120° C. |

The invention claimed is:

1. Emulsion polymer particles comprising from 29 to 41 wt % polymerized residues of at least one of acrylic acid and methacrylic acid, from 58 to 70 wt % polymerized residues of at least one $C_1$-$C_8$ alkyl (meth)acrylate and from 0.1 to 1.5 wt % polymerized residues of at least one crosslinker, wherein the particles have a Tg which occurs over a range of at least 60° C.

2. The polymer particles of claim 1 in which an average particle diameter of the polymer particles is in the range from 100 to 2000 nm.

3. The polymer particles of claim 2 in which molecular weight of the crosslinker divided by number of ethylenically unsaturated groups in the crosslinker is no greater than 150.

4. A method for producing the emulsion polymer particles by steps of: (a) providing a first monomer mixture comprising from 15 to 28 wt % of at least one $C_3$-$C_6$ carboxylic acid monomer; (b) providing a second monomer mixture comprising from 9 to 17 wt % of at least one $C_3$-$C_6$ carboxylic acid monomer; and (c) adding the first monomer mixture to a polymerization reactor while simultaneously adding the second monomer mixture to the first monomer mixture; wherein weight percentages are based on total weight of the first and second monomer mixtures.

5. The method of claim 4 in which the first monomer mixture further comprises from 54 to 74 wt % of at least one $C_1$-$C_{12}$ alkyl (meth)acrylate.

6. The method of claim 5 in which less than 5 wt % of the monomers is in the polymerization reactor prior to addition of the first monomer mixture and in which the second monomer mixture further comprises from 0.1 to 2 wt % of at least one crosslinker.

7. The method of claim 6 in which the first monomer mixture comprises from 17 to 25 wt % of at least one $C_3$-$C_6$ carboxylic acid monomer and from 58 to 70 wt % of at least one $C_1$-$C_{12}$ alkyl (meth)acrylate, and the second monomer mixture comprises from 0.1 to 1.5 wt % of at least one crosslinker.

8. The method of claim 7 in which a time of addition of the second monomer mixture to the first monomer mixture is from 75 to 100% of a time of addition of the first monomer mixture to the polymerization reactor.

* * * * *